United States Patent [19]

Swaniger et al.

[11] Patent Number: 4,520,824
[45] Date of Patent: Jun. 4, 1985

[54] INSTRUMENT FOR OPHTHALMIC LASER SURGERY

[75] Inventors: James R. Swaniger, Costa Mesa; Paul R. Goth, Irvine, both of Calif.

[73] Assignee: American Hospital Supply Corporation, Evanston, Ill.

[21] Appl. No.: 417,689

[22] Filed: Sep. 13, 1982

[51] Int. Cl.³ .............................................. A61N 5/06
[52] U.S. Cl. .................................................... 128/395
[58] Field of Search .................. 128/303.1, 362, 395, 128/645, 745; 219/121 L, 121 LA

[56] References Cited

U.S. PATENT DOCUMENTS

| | | | |
|---|---|---|---|
| 2,622,473 | 12/1952 | Littmann | 128/745 |
| 2,999,422 | 9/1961 | Papritz | 128/745 |
| 3,348,547 | 10/1967 | Kavanagh . | |
| 3,417,754 | 12/1968 | Smart | 128/395 |
| 3,567,325 | 3/1971 | Tibbals | 356/112 |
| 3,703,176 | 11/1972 | Vassiliadis et al. . | |
| 3,710,798 | 1/1973 | Bredemeier | 128/395 |
| 3,750,670 | 8/1973 | Palanos et al. | 128/303.1 |
| 3,769,963 | 11/1973 | Goldman et al. | 128/395 |
| 3,796,220 | 3/1974 | Bredemeier | 128/395 |
| 3,821,510 | 6/1974 | Muncheryan | 219/121 L |
| 3,828,788 | 8/1974 | Krasnov et al. . | |
| 3,829,791 | 8/1974 | Schwartz | 331/94.5 |
| 3,910,276 | 10/1975 | Polanyi et al. . | |
| 3,913,582 | 10/1975 | Sharon | 128/303.1 |
| 3,914,013 | 10/1975 | Rosenberg | 350/96 B |
| 3,947,688 | 3/1976 | Massey | 250/495 |
| 4,069,823 | 1/1978 | Isaka et al. | 128/303.1 |
| 4,164,222 | 8/1979 | Prokhorov et al. . | |
| 4,270,845 | 6/1981 | Takizawa et al. | 350/299 |
| 4,309,998 | 1/1982 | Aron nee Rosa et al. . | |
| 4,313,093 | 1/1982 | Suenaga et al. | 128/303.1 |

FOREIGN PATENT DOCUMENTS 8102613  1/1982  Netherlands ..................... 128/303.1

Primary Examiner—Edward M. Coven
Assistant Examiner—Max F. Hindenburg
Attorney, Agent, or Firm—Gordon L. Peterson

[57] ABSTRACT

An instrument for ophthalmic laser surgery is disclosed, in which lasers are mounted for conjoint movement with a slit lamp on an X-Y table. The laser beams are directed into the patient's eye by a beam-directing assembly which pivots together with the slit lamp's microscope about a common axis, and which receives the laser beams along that common axis. The resulting structure greatly improves the ease of use of the laser arrangement and keeps the laser beams in alignment with the microscope at all times.

20 Claims, 4 Drawing Figures

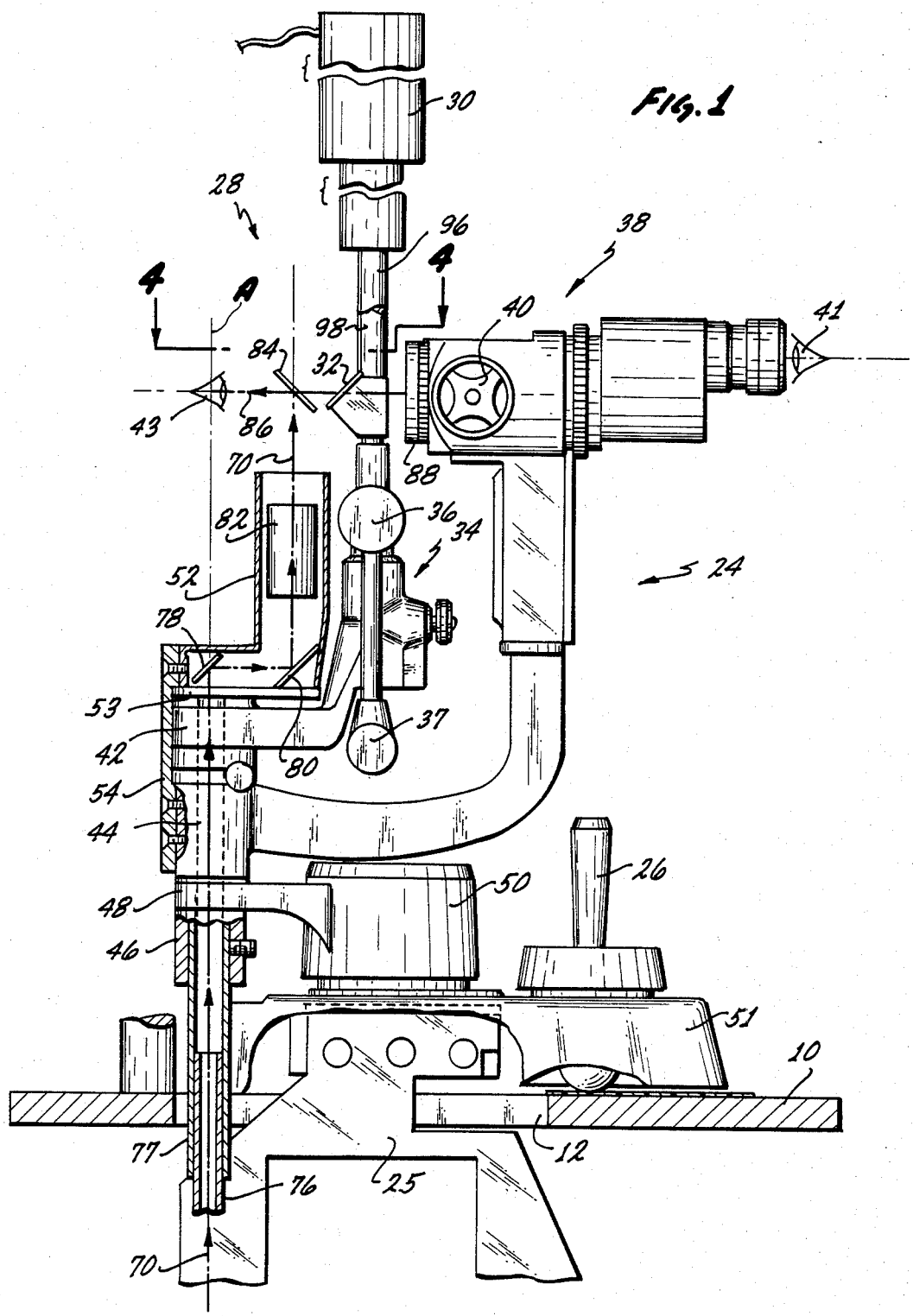

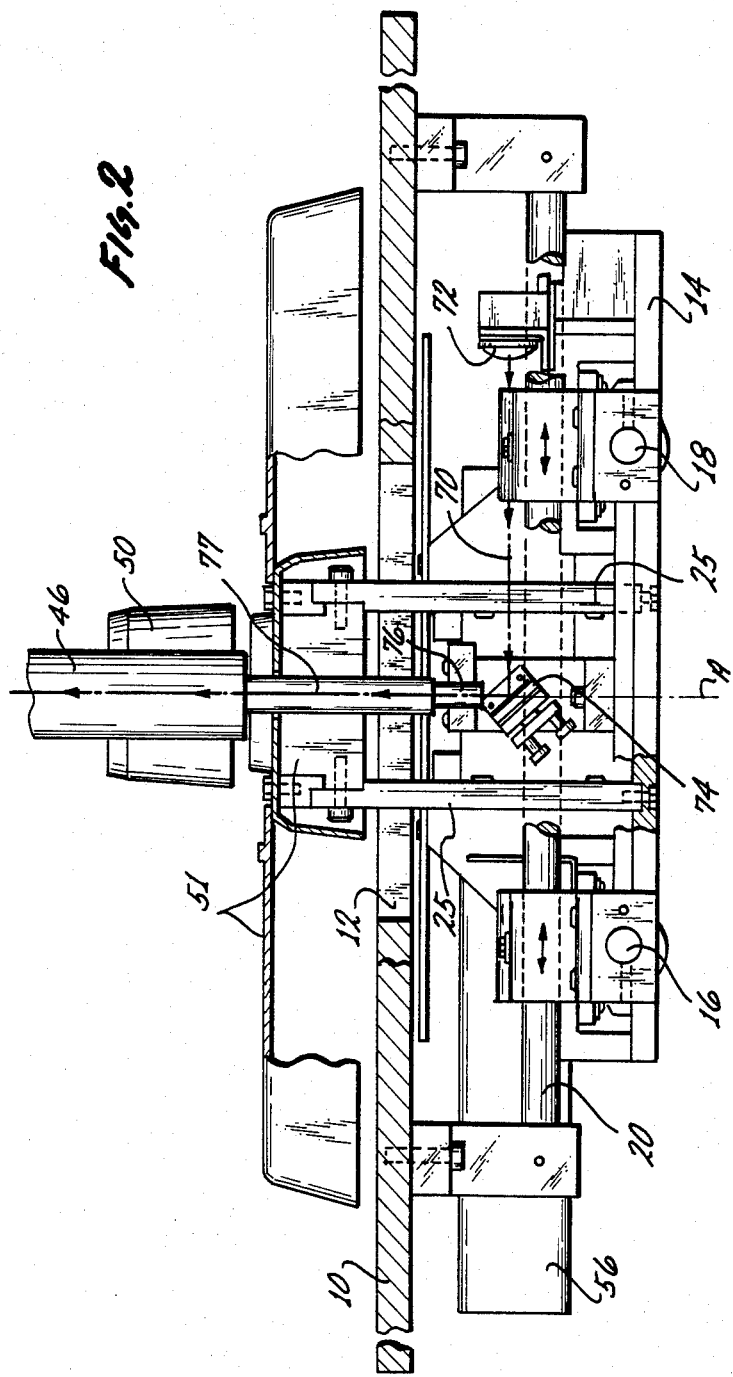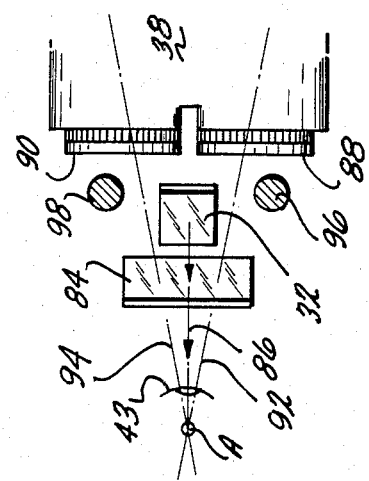

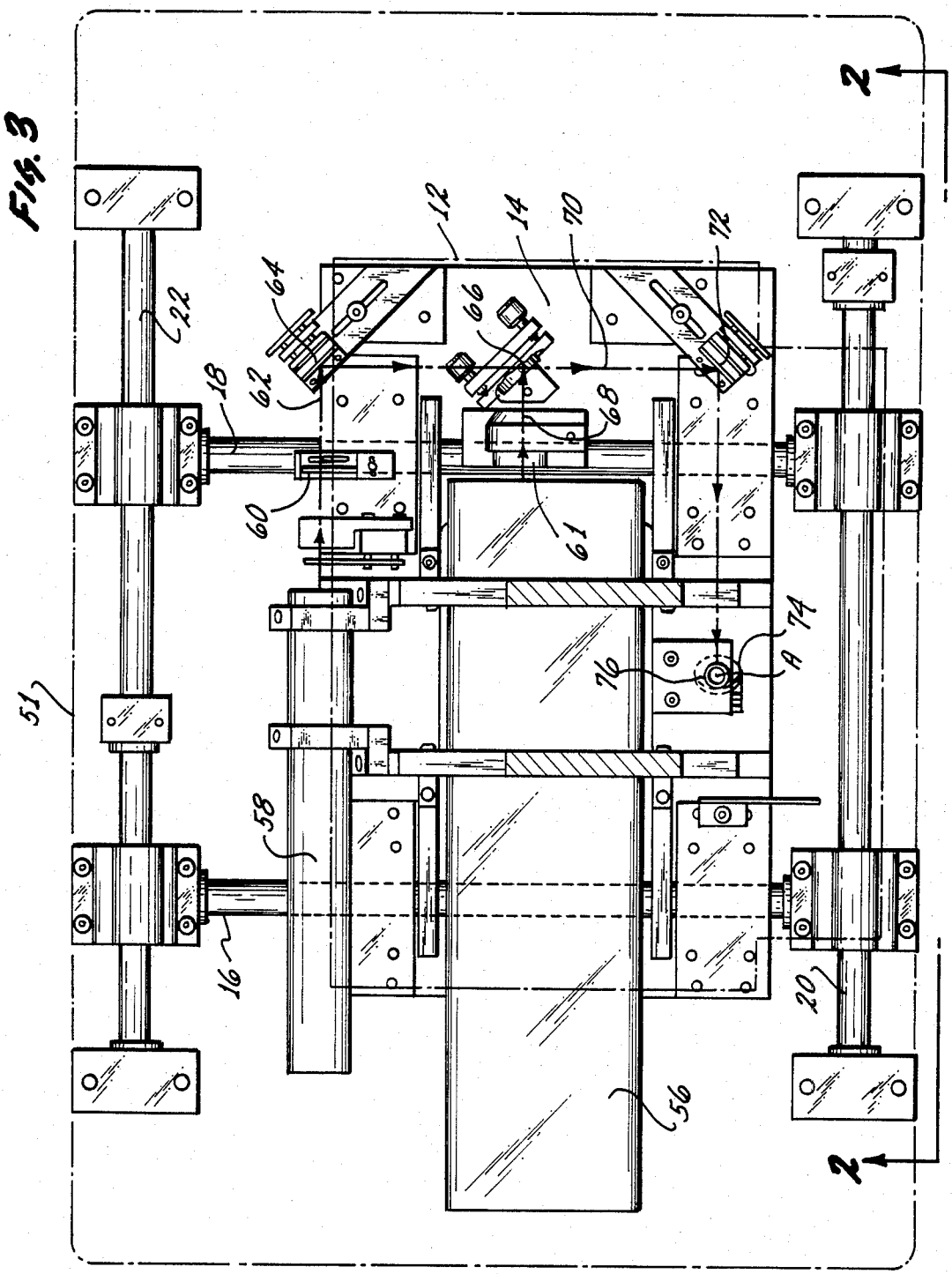

INSTRUMENT FOR OPHTHALMIC LASER SURGERY

FIELD OF THE INVENTION

This invention relates to a slit lamp with laser surgery capability for use by ophthalmic surgeons.

BACKGROUND OF THE INVENTION

In recent years, laser surgery has become an important tool for ophthalmic surgeons. The technique involves observation of the patient's eye under considerable magnification by means of a conventional slit lamp while focusing a low power visible laser beam at a desired point in the patient's eye. When the visible beam has been appropriately focused, a high-powered therapeutic beam, outside the visible spectrum but coaxial with the visible beam, is momentarily activated to cut or coagulate the tissue at the spot where the visible beam had been focused.

In the prior art (exemplified by U.S. Pat. No. 3,703,176 to Vassiliadis et al), a laser beam was produced by a laser positioned on a stationary support and connected to the slit lamp by a pair of articulated arms which allowed the slit lamp assembly to be moved into proper focus with respect to the patient's eye. In this arrangement, the laser beam used an optical path movable conjointly with the path of the light slit produced by the illuminator or light source of the slit lamp. As a practical matter, the illuminator needs to be movable with respect to the microscope of the slit lamp, through which the physician observes the eye, to permit observation of the illuminated eye from different directions. As a result, the prior art device not only failed to allow the physician to move the laser beam totally independently of the illumination column, but it also produced an annoying parallax when the microscope was not exactly aligned with the light slit beam. Inasmuch as it is often necessary for the physical to direct the light slit beam at an angle to his line of vision for better observation, the movement of the laser beam conjointly with the light slit beam created a significant problem.

In addition, the articulated arms fo the prior art required a substantial number of reflections of the laser beams by a series of mirrors. Inasmuch as this is cumbersome and makes it difficult to maintain the instrument in alignment, the use of the articulated arms considerably reduced the ease of use of the lasers.

SUMMARY OF THE INVENTION

The invention overcomes the problems of the prior art in two ways. First, the invention provides for mounting the lasers in such a way that they move conjointly with the slit light assembly. This is preferably accomplished by mounting the lasers on the same X-Y table on which the slit lamp assembly is mounted for horizontal movement with respect to its stationary support. An arrangement of that type dispenses with the need for articulated arms connecting the lasers and the slit lamp assembly, and it thereby considerably improves the instrument's maintainability and ease of use. In the arrangement of this invention, in which the lasers move with the slit lamp, the use of relatively small, light lasers is highly desirable to give the instrument a "feel" and weight comfortable to surgeons accustomed to conventional slit lamps.

Secondly, in accordance with the invention, the laser beams are directed along the pivot axis about which the microscope can be pivoted in order to observe various portions of the eye. From this axis, the laser beams are then reflected into the eye by a beam-directing system of mirrors positioned in fixed alignment with the line of sight of the microscope, and pivotable together with the microscope about the common pivot axis. As a result, the physician always looks straight down the laser beam without parallax and therfore always sees the beam as a sharply focused point.

It is therefore the object of the invention to provide a slit lamp-laser combination in which the lasers are mounted for horizontal movement conjointly with the slit lamp assembly.

It is a further object of the invention to provide for the laser beams a beam-directing means pivotable conjointly with the slit lamp microscope about a common axis, the directing means including a directing element positioned to intersect that axis.

BRIEF DESCRIPTION OF THE FIGURES

FIG. 1 is a side elevation of the modified slit lamp of this invention.

FIG. 2 is a side view, partially in section, of the X-Y table supporting the slit lamp of FIG. 1 looking in the direction of arrows 2—2 in FIG. 3.

FIG. 3 is a plan view, partially in section, of the X-Y table; and

FIG. 4 is a schematic diagram illustrating the alignment of the microscope eye pieces and the laser beams.

DESCRIPTION OF THE PREFERRED EMBODIMENT

Referring first to FIGS. 2 and 3, the apparatus of this invention is supported on a support 10 which may be a conventional equipment cabinet. The horizontal portion of the support 10 shown in FIGS. 1 and 2 is a first member of the support.

An opening 12 is formed in the surface of the support 10. An X-Y table 14 is mounted on the support 10 in the opening 12. The table 14 can be moved toward and away from the patient (i.e. up and down in FIG. 3) along guides 16, 18, and from side to side along guides 20, 22 (FIG. 2). A slit lamp assembly 24 is fixedly mounted on a movable member of the X-Y table by a pair of supporting brackets or members 25. The X-Y table 14 can therefore be moved omnidirectionally in the horizontal plane by simply pushing the slit lamp assembly 24 mounted on it (FIG. 1) in any desired horizontal direction. Fine positioning of the slit lamp assembly 24 may be accomplished in a conventional manner by fine positioning means which includes a joy stick 26, the details of which are not material to this invention. Thus, the fine positioning means and the X-Y table 14 constitute a positioning apparatus or positioning means.

The slit lamp 24, with the exception of its laser-related components, is of conventional construction. For example, one suitable slit lamp for use in the invention is the Topcon Model SL-5D. In its commercial form, the slit lamp 24 includes an illumination column 28 consisting of an illuminator 30, mirror 32, and adjustment assembly 34 which permits the illumination column 28 to be pivoted about a bearing 36 by a handle 37. The slit lamp 24 further includes a microscope 38 which is preferably of the binocular type and whose magnification can be changed by a control knob 40. The physician 41 observes the patient's eye 43 through the microscope 38.

In the commercial slit lamp 24, the illumination column 28 and microscope assembly 38 are pivotally mounted by bearings 42, 44, respectively, for independent pivotal movement about a pivot shaft 46 mounted in a bracker 48 attached to a foot 50. The pivot shaft axis A is so positioned as to normally pass through the target area of the patient's eye 43. The foot 50 is provided with a conventional adjustment mechanism (not shown) which permits the entire slit lamp assembly 24, including the foot 50, to be moved up and down with respect to the base 51 attached to table 14 by the brackets 25.

In accordance with the invention, the pivot shaft 46 is hollowed out to form an open-ended cylinder, and a beam-directing assembly 52 (described in greater detail below) is mounted by a bearing 53 for pivotal movement about the open top of pivot shaft 46. A connecting plate 54 interconnects the beam-directing assembly bearing 53 and the microscope assembly bearing 44 so as to cause the beam-directing assembly 52 and the microscope assembly 38 to move together as a unit.

Referring now to FIG. 3, a high-powered therapeutic laser 56 and a low-powered aiming laser 58 are mounted on the X-Y table 14. Typically, the therapeutic laser 56 may be a Nd:YAG laser operating in the non-visible 1064 nm wavelength range. The aiming laser 58 may be a HeNe laser operating the 638 nm range of visible light. In accordance with conventional techniques, the beam from aiming laser 58 is passed through a beam spreader 60 to allow subsequent focusing. A similar beam spreader 61 is provided in front of the therapeutic laser 56.

The aiming beam 62 is reflected by a mirror 64 mounted on the X-Y table 14 and is then passed through a dichroic combiner mirror 66 where it is coaxially combined with the therapeutic beam 68. The combined beam 70 (which, at different times, may consist of beam 62, beam 68, or both) is reflected by a mirror 72 mounted on the table 14 to a point underneath the center of the pivot shaft 46 (FIG. 1). At that point it is upwardly reflected by a mirror 74 along the axis A of pivot shaft 46. The beam 70 travels upwardly through tubes 76, 77, and through the hollow interior of pivot shaft 46. Tube 76 is attached to the table 14, while tube 77 is concentrically attached to pivot shaft 46. The tubes 76, 77 telescope with respect to one another in order to accommodate vertical movement of the slit lamp assembly 24 with respect to the table 14.

As best shown in FIG. 1, the beam-directing assembly 52 includes a pair of mirrors 78, 80 which are mounted on the assembly 52. The mirror 78 intercepts the pivot shaft axis A, where the combined beam 70 impinges upon it. The beam 70 is reflected toward mirror 80, which in turn reflects the beam 70 into conventional laser optics 82 which are also mounted on assembly 52. The optics 82 are conventionally adjustable to focus the beam 70 on the axis A within the patient's eye 43. Exiting from the optics 82, the beam 70 is reflected into the patient's eye 43 by a dichroic mirror 84 which is also mounted on the beam-directing assembly. The mirror 84 is so designed, by conventional optical techniques, as to pass through to the microscope 38 the visible laser light of aiming beam 62 which is reflected from the patient's eye 43, but to prevent the passage to the microscope 38 of any reflections of the therapeutic beam 68 from the eye 43.

Referring now jointly to FIGS. 1 and 4, it will be observed that inasmuch as the beam-directing assembly 52 pivots conjointly with microscope 38 about the axis A of pivot shaft 46, the dichroic mirror 84 as well as the horizontal portion 86 of the combined beam 70 will always be precisely aligned and centered with respect to the microscope eyepieces 88, 90. Consequently, there can be no parallax in the observation of the laser beam by the physician.

FIG. 4 illustrates the fact that the light slit beam from illuminator 30 is reflected by a mirror 32 which, being part of the illumination column, can move with respect to the microscope 38. The mirror 32 directs the light slit into the patient's eye 43 but is not within the line of vision of either of the eyepieces 88, 90. The light slit illuminating the patient's eye, as well as the focal point of the aiming laser beam 62, is observed by the two eyepieces of the microscope 38 along lines 92, 94 respectively. The illuminator 30 is typically supported by rods 96, 98 which are also positioned outside the field of vision of eyepieces 88, 90.

We claim:

1. An instrument for ophthalmic laser surgery, comprising:
   (a) a slit lamp adapted to be positioned adjacent a patient's eye, said slit lamp including magnifying means for observing said eye, and said magnifying means being mounted for pivotal movement about an axis;
   (b) laser means for producing a beam of laser light;
   (c) beam-directing means for directing said laser beam into said eye, said beam impinging upon said beam-directing means along said axis;
   (d) means for pivotally mounting said beam-directing means for pivotal movement coaxial with said magnifying means and coupling means for coupling the magnifying means and the beam-directing means for pivotal movement together about said axis; and
   (e) said slit lamp including an illuminator for providing an illumination beam for the patient's eye and means for mounting the illuminator for pivotal movement relative to said beam-directing means and said magnifying means.

2. The instrument of claim 1, in which said beam-directing means include first mirror means positioned to intercept said axis so as to reflect said beam in a lateral direction, second mirror means positioned to reflect said beam from said lateral direction into a direction generally parallel to said axis, and third mirror means positioned to reflect said beam form said generally parallel direction into a patient's eye.

3. The instrument of claim 2, in which said third mirror means are fixedly positioned in alignment with, and within the field of vision of, said magnifying means.

4. The instrument of claim 3, in which said third mirror means are partially transparent to visible aiming laser light but totally reflective to therapeutic laser light outside the visible spectrum.

5. The instrument of claim 1, in which said laser means include an aiming laser and a therapeutic laser, and in which combining means are provided to convey the beams of both said lasers to said beam-directing means coaxially of each other.

6. The instrument of claim 1, in which said axis is defined by pivot shaft means on which said magnifying means and said beam-directing means are pivotally supported for conjoint pivotal movement.

7. The instrument of claim 6, in which said pivot shaft means are in the form of a hollow cylinder, said laser beam being conveyed along said axis through the interior of said hollow cylinder.

8. The instrument of claim 1, wherein said means for pivotally mounting the illuminator mounts the illuminator for pivotal movement about said axis.

9. The instrument of claim 8 wherein the instrument includes a support and means for mounting said slit lamp said laser means and said beam-directing means on said support for conjoint movement relative to the support.

10. The instrument of claim 9 wherein said mounting means includes an X-Y table.

11. The instrument of claim 1 wherein said mounting means for the beam-directing means includes a shaft and a first bearing coupled to the beam-directing means and rotatably mounted on the shaft, said instrument includes a second bearing rotatably mounted on the shaft and coupled to the magnifying means and said coupling means includes a connector drivingly coupling said bearings.

12. An instrument for ophthalmic laser surgery comprising:
(a) a support;
(b) a positioning apparatus supported by the support and having a movable member movable in a generally horizontal plane;
(c) laser means for producing a beam of laser light, said laser means being carried by said movable member and movable therewith in the generally horizontal plane;
(d) first means carried by said movable member and movable therewith in the generally horizontal plane for directing the laser beam from the laser and including a beam-directing apparatus for directing the laser beam to an eye of a patient;
(e) a slit lamp carried by said movable member and movable therewith in the generally horizontal plane;
(f) said slit lamp including magnifying means for observing the eye of the patient and an illuminator for providing an illumination beam for the patient's eye;
(g) means for mounting the magnifying means and the beam-directing apparatus for pivotal movement about an axis and coupling means for coupling the magnifying means and the beam-directing apparatus for pivotal movement together about said axis;
(h) means for mounting the illuminator for pivotal movement relative to the beam-directing apparatus and the magnifying means; and
(i) said first means directing the laser beam along said axis.

13. The instrument of claim 12 wherein said illuminator mounting means mounts the illuminator for pivotal movement relative to the beam-directing apparatus and the magnifying means about said axis.

14. The instrument of claim 13 wherein the support includes a first member and said movable member and said laser means are below said first member of said support and the slit lamp is above said first member of said support.

15. The instrument of claim 14 wherein the first member of the support has an opening and said mounting means for the magnifying means and the beam-directing apparatus extends through said opening, and said first means directs the laser beam through at least part of the mounting means for the magnifying means and the beam-directing apparatus.

16. An instrument for ophthalmic laser surgery comprising:
a slit lamp including magnifying means for observing the eye of a patient and an illuminator for providing an illumination beam for the patient's eye;
a laser for producing a laser beam;
means for supporting said laser below said slit lamp;
beam-directing means for directing the laser beam to the patient's eye;
said slit lamp including means for mounting the illuminator for pivotal movement relative to the laser; and
positioning means for positioning the slit lamp, the laser and the beam-directing means together as a unit 17. An instrument as defined in claim 16 wherein said positioning means includes fine-positioning means for fine positioning of the slit lamp, said positioning means includes an X-Y table below said fine-positioning means and said slit lamp, laser, beam-directing means and fine-positioning means being carried by said X-Y table.

18. An instrument as defined in claim 17 including a member extending between said X-Y table and said fine-positioning means and said X-Y table being mounted on the member.

19. An instrument as defined in claim 18 including a support, said slit lamp being carried by said support and said laser being below said support and said positioning means includes means above said support for positioning said slit lamp relative to said support.

20. An instrument as defined in claim 16 wherein the positioning means includes an X-Y table, said laser is a therapeutic laser and said laser beam is a therapeutic laser beam, said instrument includes an aiming laser which provides a visible laser beam, said lasers are carried by said X-Y table and are below said slit lamp, said beam-directing means includes means below said slit lamp for directing both of said laser beams upwardly and means for directing the upwardly directed laser beams to the patient's eye.

* * * * *